United States Patent [19]
Komoto et al.

[11] Patent Number: 4,868,191
[45] Date of Patent: Sep. 19, 1989

[54] ALKALOID COMPOUNDS, AND PHARMACEUTICAL COMPOSITIONS CONTAINING THEM

[75] Inventors: Shigeo Komoto, Konakadai, Japan; Y. A. Gunawardana, Vero Beach, Fla.

[73] Assignee: Harbor Branch Oceanographic Institution, Inc., Ft. Pierce, Fla.

[21] Appl. No.: 168,883

[22] Filed: Mar. 3, 1988

[51] Int. Cl.$^4$ .................. A61K 31/47; C07D 513/16; C07D 471/06
[52] U.S. Cl. ................................. 514/280; 514/287; 546/48; 546/72
[58] Field of Search .............. 546/48, 72; 514/280, 514/287

[56] References Cited

U.S. PATENT DOCUMENTS 4,555,572 11/1985 Capps ..................................... 546/14
4,631,149 12/1986 Rinehart, Jr., et al. ............ 540/546

FOREIGN PATENT DOCUMENTS 0000198 1/1988 World Int. Prop. O. .......... 540/478

OTHER PUBLICATIONS

Sakai et al., J. Am. Chem. Soc., vol. 108(20), pp. 6405–6405 (10/01/86).
Nakamura et al., Tetrahedron Letters, vol. 28, no. 6, pp. 621–624 (02/87).
Gunawardana et al., J. Am. Chem. Soc., vol. 110(14), pp. 4856–4858 (1988).

Primary Examiner—Mukund J. Shah
Assistant Examiner—Diana G. Rivers
Attorney, Agent, or Firm—Carroll F. Palmer

[57] ABSTRACT

Novel alkaloid compounds that are derivatives of methaniminoetheno[d,e]acridine are derived from marine sponges of the genus Dercitus. These compounds and pharmaceutical compositions containing therapeutic effective amounts thereof are useful as antitumor and immunomodulatory medications.

8 Claims, No Drawings

ALKALOID COMPOUNDS, AND PHARMACEUTICAL COMPOSITIONS CONTAINING THEM

FIELD OF THE INVENTION

This invention relates to new organic compounds and compositions which have useful therapeutic properties. More particularly, the invention relates to novel alkaloid compounds derived from a marine organisms, i.e., a sponge of the family Pachastrellidae, genus Dercitus, pharmaceutical compositions comprising such compounds and their methods of use for therapeutic purposes.

BACKGROUND OF THE INVENTION

Various tumor related diseases inflict man and other mammals and, as these conditions are often fatal, the prevention, control of growth and regression of tumors in mammals has been receiving widespread attention by the medical profession and pharmaceutical industry. The term tumor refers to abnormal masses of new tissue growth which is discordant with the economy of the tissue of origin or the host's body as a whole.

Tumors inflict mammals and man with a variety of disorders and conditions including various forms of cancer and resultant cancerous cachexia, which term refers to the symptomatic discomfort that accompanies the infliction of a mammal with a tumor. Such symptoms include weakened condition of the inflicted mammal as evidenced by weight loss, etc. The seriousness of cancer is well known since cancer is a major cause of death in man.

Considerable research and resources have been devoted to oncology and antitumor measures including chemotherapy. While various antitumor agents and methods have been developed which aid in inhibiting tumors, additional methods and chemical agents are needed.

A potential source for antitumor compounds is marine plants and animals. In fact, marine sponges have proved to be a productive source for such compounds. The present invention has added to the arsenal of antitumor substances by the discovery of new organic compounds possessing useful antitumor activity isolated from extracts of sponge of the genus Dercitus.

OBJECTS

A principal object of this invention is the provision of new organic compounds and compositions comprising such compounds.

Additional objects are the provision of methods for producing the new compounds and compositions.

Yet another object is the provision of methods of using the new compounds and compositions, particularly, methods for treating ailments associated with tumors, viruses, fungus growth and to modify the immune system.

Additional objects and the full scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The objects are accomplished, in part, by the discoveries of the invention which have provided novel compounds of the formula I:

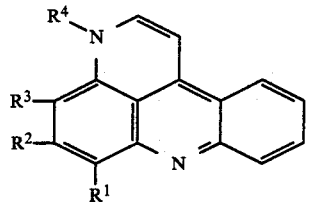

wherein:
R$^1$ is a group selected from —CH$_2$CH$_2$N(CH$_3$)$_2$; —CH$_2$CH$_2$N+(CH$_3$)$_3$X−; —CH$_2$CH$_2$N+(O−)(CH$_3$)$_2$; —CH=CH$_2$; —CHO; and —COOR, X is halogen, R is hydrogen or lower alkyl, i.e., C1-C5 alkyl, R$^2$ is hydrogen or together with R$^3$ is —N=CZ—S—, R$^3$ together with R$^2$ is —N=CZ—S— or is a group selected from —NH$_2$, —NHCOR, and hydrogen, and Z$_4$ is —NO$_2$, —NH$_2$, or hydrogen.

R$^4$ is hydrogen or lower alkyl, and

The invention also provides the dihydro and tetrahydro derivatives of the above compounds according to the formulae II and III:

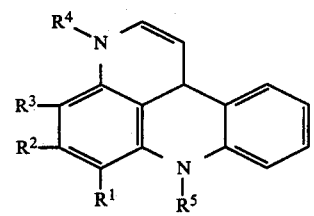

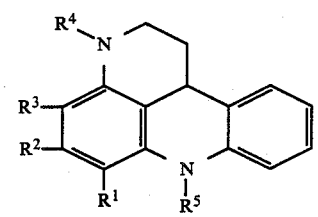

wherein R$^5$ is a group selected from hydrogen, lower alkyl, or lower alkanoyl, i.e., C1-C5 alkanoyl and the other substituents have the meaning noted above.

Preferred compounds of the invention are those of the formula IV in which the substituents are as noted above:

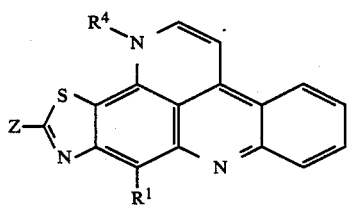

and the dihydro and tetrahydro derivatives thereof.

In preferred embodiments of the invention, the new compounds are substantially pure.

Also provided by discoveries of the invention are pharmaceutical compositions containing between about 1–45%/w of one of the new compounds of the invention or a mixture of two or more of such compounds and one or more pharmaceutically acceptable carrier or diluent.

The invention provides a variety of processes for the production of compounds of the invention. A preferred method of producing compounds of the formula I comprises the steps of collecting marine sponge of the genus Dercitus, contacting such sponge with a selected organic solvent system to obtain an extract, fractioning the extract and isolated alkaloid compounds of formula I from the fractionated extract.

In further preferred methods of the invention, compounds of the formulae II and III are made by hydrogenation of the compounds I in the presence of a hydrogenation catalyst. Also, Wurtz-Fittig, Grignard and other known synthesis type reactions may be used pursuant to known procedures to add or modify various groups in the preferred compounds to produce other compounds according to the formulae I–III.

As a result of the discoveries by the invention of the new compounds, skilled chemists will also be able to use known procedures to synthesize these compounds from available stock substances.

The objects are further accomplished according to the invention by the discovery that tumors can be inhibited by contacting cells of the tumor with an effective amount of the new compounds and, further, that cancerous cachexia caused by the presence of a tumor in a mammalian host can be treated by contacting cells of the tumor with the new compounds.

DESCRIPTION OF THE PREFERRED EMBODIMENTS

A more complete understanding of the invention can be obtained by reference to preferred embodiments of the invention which are illustrated by the following specific examples of compounds, compositions and methods of the invention. It will be apparent to those skilled in the art that the examples involve use of materials and reagents that are commercially available from known sources, e.g., chemical supply houses, so no details are given respecting them.

EXAMPLE 1

This example concerns the preparation of dercitin 1, i.e., the compound of the formula V:

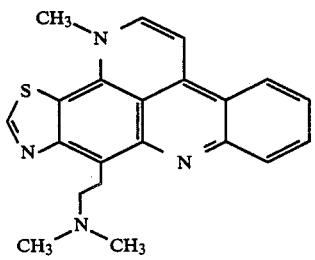

Marine sponge of the genus Dercitus was collect at a depth of 700 feet in Goulding Cay, Bahamas. The sponge is dark purple both alive and preserved in ethanol; it appears dark purple, red-purple, or black underwater. It is lobate to thinly encrusting, from 1–10 mm thick. It occurs as patches about 5–10 cm across. The surface of the sponge is smooth. The consistency is dense and firm.

Identification of the sponge to the family Pachastrellidae and genus Dercitus is based on microscopic examination of the taxonomic voucher specimens one of which has been deposited with the Indian River Coastal Zone Museum (Catalog No. 003:00040), Harbor Branch Oceanographic Institution, Inc, Ft. Pierce, Fla.

The ectosomal skeleton is a crust of spicules (both megascleres and microscleres); the choanosomal skeleton is a dense mass of megascleres and microscleres. There is no spongin. Megascleres are plagiotriaenes or calthrops, some with dichotomous clads. The rhabd is 100–300 μm in length; the clads are 70–200 μm in length. The megascleres are calthrops with nearly isoactine rays, 100–150 μm in length. Microscleres are sanidasters, 10–14 μm in length. An extract of the sponge is prepared by homogenizing the 97 gram frozen sponge and extracting it successively with ethyl acetate and methanol. A 2.0 gram portion of the crude extract from the methanol extraction is fractionated by multilayer planetary coil, countercurrent chromatographic apparatus using a 5:10:6 methylene chloride/methanol/water mixture as the mobile, upper phase. A violet-colored fraction with a retention volume of 308 to 408 ml was separated at 800 rpms. with a flow rate of 4 mm/min. to yield 29 mg. of the violet colored compound, dercitin 1.

Further purification is carried out with high-pressure liquid chromatography using a 10×250 mm aminopropyl, 7 micron particle size column employing a mixture of 30% methylene chloride in methanol as the eluent.

In an alternate procedure, 135 g of the sponge is treated as just described, but the residue of the sponge is homogenized with chloroform or methylene chloride and aqueous $NH_4OH$. The resulting organic phase is repeatedly extracted with 10% $H_2SO_4$. The aqueous phase is basified and re-extracted with chloroform or methylene chloride to give a crude preparation of dercitin 1. This is further purified by countercurrent chromatography using the organic layer from a methanol, methylene chloride and water mixture (5:5:3) as the stationary phase and the aqueous phase made of N/1000 $H_2SO_4$ as the mobile phase at 800 rpm. The eluent fractions from 340 to 960 ml. are concentrated, basified with aqueous ammonium hydroxide and extracted with methylene chloride to give dercitin 1 (0.360 g.).

Using typical spectral measurement techniques and apparatus, the following spectral data are determined for dercitin 1:

Mass: HREI 360.1398 ($M^{+\circ}$, $C_{21}H_{20}N_4S$, −2.7 mmu)
HRFAB 361.11514 ($M^{+}+H$, $C_{21}H_{21}N_4S$, −2.7 mmu)

$^1$H NMR ($CD_3OD$, 360 MHz) δ8.84 (1H, s), 7.70 (1H, d, J=7.0 Hz), 7.65 (1H, d, J=8.3 Hz), 7.06 (1H, dd, J=8.3, 6.6 Hz), 6.96 (1H, d J=8.3 Hz), 6.51 (1H, dd J=8.3, 6.6 Hz), 4.15 (3H, s), 2.78 (2H, t, J=5.7 Hz), 2.52 (2H, t, J=5.7 Hz), 2.41 (6H, s).

$^{13}$C NMR (TFA-d, 90.56 MHz) δ151.9 (d), 150.9 (s), 149.3 (d), 148.2 (s), 141.1 (s), 138.2 (d), 136.6 (s), 135.5 (s), 126.5 (d), 126.5 (d), 122.0 (s), 119.1 (d), 116.4 (s), 109.8 (d), 56.5 (t), 51.4 (q), 45.2 (q), 28.5 (t).

UV λmax (MeOH) 245 nm (ε=13800), 307 (16900), 541 nm (1800); max (MeOH+H$^+$) 234 nm (ε=13800), 245 (14500), 307 (19500), 354 (4500), 515 nm (3300); λmax (MeOH+OH$^-$) 206 nm (ε 19500), 238 (12600), 261 (11750), 293 (14450), 405 (6000), 527 (2050), 558 (1750) and 610 nm (1550).

EXAMPLE 2

The following assay methods are utilized to evaluate the antitumor activity of the alkaloid compounds of the invention.

P338 Mouse Leukemia Cell Assay

Maintenance of Cell Lines

P338 mouse leukemis cells are grown in Dulbecco MEM medium with 10% horse serum, 4 mM glutamine, and 20 ug/ml gentamycin (Biologos, Inc.). Cells are incubated in humidified air containing 10% $CO_2$ at 37° C. and subcultured 2 time per week.

Procedure

1. Add compound to each well of a 24-well plate to tube and allow solvent to evaporate to dryness.
2. Add 2 ml ($1.2 \times 10^5$) cells to each well or tube and mix.
3. Incubate in 10% $CO_2$ at 37° C. for 48 hours.
4. Read plates with an inverted microscope, scoring activity from 1+ to 4+ as follows: ND (not detectable), 90% 1+, 75-90% 2+, 50-74% 3+, 25-49% 4+, 25% of control growth.

Alternatively, the activity may be designated as $IC_{50}$ concentration which is the concentration of compound required to inhibit 50% of cell growth on the plate.

Cell counts are performed on each tube and results are reported as percent of control.

Human Tumor Cell Line Assay

Maintenance of Cell Lines

HCT-8 human colon tumor cells are grown in RPMI 1640 medium. A-549 human lung carcinoma cells are grown in Dublecco MEM medium. T-47D human breast cancer cells are cultured in Eagles MEM medium. All media (Biologos, Inc.) are supplemented with 10% fetal bovine serum and contain 50 ug/ml gentamicin. All humand tumor cell lines are incubated in humidified air containing 5% $CO_2$ at 37° C. and subcultured once a week. The seeding levels are 200,000 T-47D cells, 60,000 HCT-8 cells and 300,000 A-549 cells per T-25 Flask. Vinblastine is used as a positive control.

Procedure

1. Seed 1 ml containing 5000 HCT-8, 2000 A-549, or 1500 T-47D cells in each well of a 24-well plate.
2. Incubate is a $CO_2$ incubator for 48 hours.
3. Add compound to each well and incubate for an additional 120 hours.
4. Discard medium and stain with methylene blue (HCT-8) or crystal violet (A-549 and T-47D).
5. Compare cell density of compound-treated with that of the control (no compound added) as follows: ND (not detectable), 90% 1+, 75-90% 2+, 50-74% 3+, 25-49% 4+, 25% of control growth.

The positive control is Vinblastine in aqueous solution at the following concentrations:

| Solution Conc. | | Amount Added | Final Test Conc. | |
|---|---|---|---|---|
| 5 | mg/ml | 2 ul | 5 | ug/ml |
| 1 | mg/ml | 2 ul | 1 | ug/ml |
| 0.1 | mg/ml | 2 ul | 0.1 | ug/ml |
| 0.05 | mg/ml | 2 ul | 0.05 | ug/ml |

The results of the above assays are summarized in Table I.

TABLE I

| Antitumor Activity of Dercitin 1 | | | |
|---|---|---|---|
| Mouse P388: in vitro $IC_{50}$ = 0.05 ug/ml | | | |
| in vivo T/C 170% at 5 mg/kg | | | |
| Human Cell Line Data: | | | |
| ug/ml | HCT-8 | A-549 | T-47D |
| 2 | 4+ | 4+ | 4+ |
| 1 | 4+ | 4+ | 4+ |
| In-Vivo P388 protocol: | | | |
| ug/ml | HCT-8 | A-549 | T-47D |
| 0.1 | 4+ | 4+ | 4+ |
| 0.01 | ND | ND | ND |

The data of Table I reports in vitro activity of compounds of the invention for inhibiting tumors. These results indicate, as will be apparent to those skilled in the art, that the compound dercitin 1 and the other alkaloids of the invention are useful for inhibiting tumors in vivo in hosts, including mammals, for treating diseases caused thereby.

EXAMPLE 3

This example concerns tetrahydrodercitin 1 which is represented by the following formula VI:

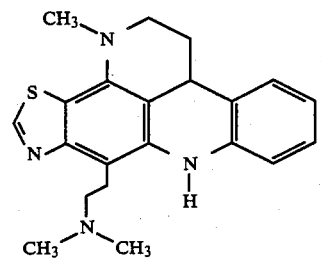

VI

A portion of dercitin 1 and a small amount of hydrogenation catalyst, e.g., Pd/C, Pt/C or Raney Ni are mixed in a suitable solvent, e.g., ethanol or methanol. The mixture is stirred in the presence of hydrogen in a hydrogenation apparatus capable of operation at elevated pressure, e.g., Parr apparatus, to produce tetrahydrodercitin 1. If the reaction is too slow, it is facilitated by making the media slightly acidic by addition of a trace amount of HCl or like acid. Partial reduction to dihydrodercitin 1 can be attained by hydrogenation at ambient pressure conditions.

EXAMPLE 4

This example concerns immunomodulatory activity of compounds of the invention on murine derived, two-way mixed lymphocyte reaction assay.

| Conc. ug/well | % MLR | % LCV |
|---|---|---|
| Immunomodulatory activity of Dercitin 1. | | |
| 10.0 | 0 | 67 |
| 1.0 | 0 | 46 |
| 0.1 | 0 | 48 |

| Conc. ug/well | % MLR | % LCV |
|---|---|---|
| 0.01 | 0 | 56 |
| Immunomodulatory activity of Tetrahydrodercitin 1. | | |
| 10.0 | 0 | 41 |
| 1.0 | 0 | 49 |
| 0.1 | 0 | 91 |
| 0.01 | 0 | 100. |

Discussion of Variables

The scope of the invention is not limited by the specific examples and suggested procedures and uses related herein since modifications can be made within such scope from the general information provided by this specification to those skilled in the art. In addition to hydrogenated derivatives as examplified above, fluorinated and salt derivatives may be prepared and have pharmaceutical activity. Such activity, in addition to the antitumor and immunomodulatory activity as reported, may be for analgesic applications.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include, ethanol, dimethyl sulfoxide, glycerol, silica, alumina, starch, and equivalent carriers and diluents.

While effective amounts may vary, as conditions in which such compositions are used vary, a minimal dosage required for antitumor activity is generally between 0.01 and 10 micrograms of the new compound against $10^5$ tumor cells. To provide for the administration of such dosages for the desired therapeutic treatment, new pharmaceutical compositions of the invention will advantageously comprise between about 1% and 45%, and especially 3% and 15%, by weight of one or more of the new compounds based on the weight of the total composition including the carrier or diluent.

The new compounds are active for treatment of a diverse range of tumors including, but not limited to, mouse leukemia cells, human lung, colon, and mammary tumor cells. The new compounds are also useful for the treatment of cancerous cachexia and as immunomodulatory agents. An intended use is for immune reactions (invivo/invitro) that require modulation via T-cell activity. Direct application would be for human invivo suppression of T-cell responses, e.g., transplantation and autoimmunity.

In preferred embodiments for production of the new compounds by extraction from marine sponges, etc., suitable organic solvent systems for extraction can be selected from methanol, ethyl acetate, toluene, heptane, hexane, isooctane, acetone, benzene, diethyl ether, t-butyl methyl ether, ethanol, isopropanol, 1,2 dichloroethane and especially, chloroform, ammonium hydroxide and dichloromethane. Mixtures of two or more of such solvents in various ratios and combinations are advantageous.

Compounds of the invention are synthesized and/or isolated by various fractionation and chromatographic techniques from the extracts obtained as disclosed. Preferred isolation procedures include various chromatography techniques, e.g., countercurrent chromatography with suitable columns, including multi-layer planetary coil columns. A variety of solvents are available for use as single or mixed elutents, such as methylene chloride, methanol, ethyl acetate, acetonitrile, n-propanol, n-butanol, water, dilute sulfuric acid, and equivalent solvents. Further purifications using such procedures may also be carried out on the recovered extractions. Preferred isolation techniques for further purification include chromatographic operations such as high-pressure, liquid chromatography with suitable columns with suitable solvent, particularly, methylene chloride/methanol or methanol/water mixtures.

By way of example of synthesis methods to convert the —N=CH—S— group of dercitin 1 into $R^2$=H and $R^3$=H or —NH$_2$, dercitin 1 is reduced using Raney Ni catalyst. Then to convert $R^3$ from —NH$_2$ into —NHCOR, acylation is preformed using ROCl. To convert Z from —H to —NO$_2$, one reacts dercitin 1 with HNO$_3$/HOAc and the resulting nitro derivative can be reacted with Na borohydride or lithium aluminum hydride to provide Z=—NH$_2$. To convert $R^1$ from —CH$_2$CH$_2$N(CH$_3$)$_2$ to —CH$_2$CH$_2$N$^+$(CH$_3$)$_3$X$^-$ one methylates dercitin 1, e.g., with MeI, and the resulting derivative salt can be converted by Hoffman degradation into $R^1$=—CH=CH$_2$, which, in turn, by ozonolysis or periodate oxidation converts $R^1$ into —CHO or —COOH. The latter, by esterification turns $R^1$ into —COOR. Also, to convert $R^1$ into —CH$_2$CH$_2$N$^+$(O$^-$)(CH$_3$)$_2$ one performs peracid oxidation on dercitin 1. To provide $R^5$=lower alkyl, one reacts dercitin 1 with RX (alkyl halide) and to provide $R^5$=lower alkanoyl one reacts dercitin 1 with RCOCl (acyl chloride). Similar synthesis reactions may be applied to dihydrodercitin 1 and tetrahydrodercitin 1.

The embodiments of the invention in which an exclusive property or privilege is claimed are defined as follows:

1. A substantially pure compound of the formula selected from the formulae I, II or III:

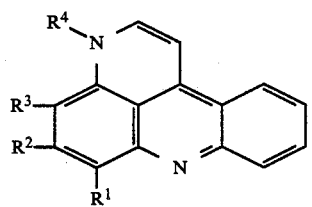

I

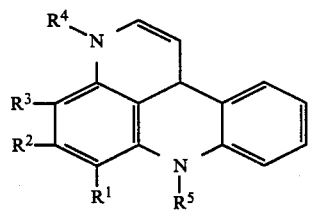

II

-continued

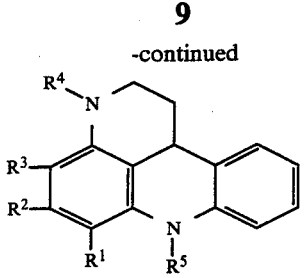

wherein:
R¹ is a group selected from —CH₂CH₂N(CH₃)₂; —CH₂CH₂N+(CH₃)₃X⁻; —CH₂CH₂N+(O⁻)(CH₃)₂; —CH=CH₂; —CHO; and —COOR,
X is halogen,
R is hydrogen or lower alkyl, i.e., C1–C5 alkyl,
R² is hydrogen or together with R³ is —N=CZ—S—,
R³ together with R² is —N=CZ—S— or is a group selected from —NH₂, —NHCOR, and hydrogen, and
Z is —NO₂, —NH₂ or hydrogen,
R⁴ is hydrogen or lower alkyl, and
R⁵ is a group selected from hydrogen, lower alkyl, or lower alkanoyl.

2. A substantially pure compound of the formula:

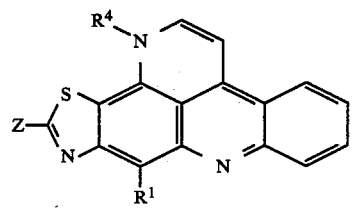

wherein:
R¹ is a group selected from —CH₂CH₂N(CH₃)₂; —CH₂CH₂N+(CH₃)₃X⁻; —CH₂CH₂N+(O⁻)(CH₃)₂; —CH=CH₂; —CHO; and —COOR,
X is halogen,
R is hydrogen or lower alkyl, i.e., C1–C5 alkyl,
Z is —NO₂, —NH₂ or hydrogen,
R⁴ is hydrogen or lower alkyl.

3. A pharmaceutical composition comprising between about 1% and 45% by weight based on the total weight of said composition as an active ingredient one or more compounds of claim 1 and a non-toxic pharmaceutically acceptable carrier or diluent.

4. A pharmaceutical composition comprising between about 1% to 45% by weight based on the total weight of said composition as an active ingredient one or more compounds of claim 2 and a non-toxic pharmaceutically acceptable carrier or diluent.

5. The substantially pure compound of the formula:

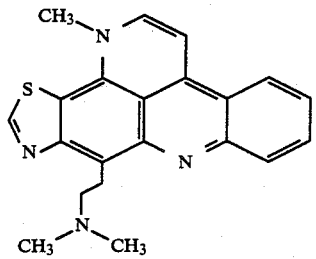

6. A pharmaceutical composition comprising between about 1% to 45% by weight based on the total weight of said composition as an active ingredient the compound of claim 5 and a non-toxic pharmaceutically acceptable carrier or diluent.

7. The compound of the formula:

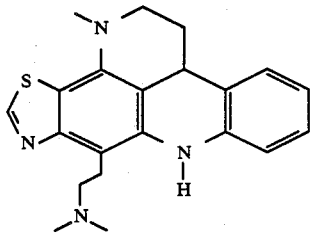

8. A pharmaceutical composition comprising between about 1% to 45% by weight based on the total weight of said composition as active ingredient the compound of claim 7 and a non-toxic pharmaceutically acceptable carrier or diluent.

* * * * *